(12) United States Patent
Ferree

(10) Patent No.: US 7,338,525 B2
(45) Date of Patent: *Mar. 4, 2008

(54) METHODS AND APPARATUS FOR PREVENTING THE MIGRATION OF INTRADISCAL DEVICES

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 649 days.

This patent is subject to a terminal disclaimer.

(21) Appl. No.: 10/426,995

(22) Filed: Apr. 30, 2003

(65) Prior Publication Data

US 2003/0204260 A1 Oct. 30, 2003

Related U.S. Application Data

(60) Provisional application No. 60/376,505, filed on Apr. 30, 2002.

(51) Int. Cl.
*A61F 2/44* (2006.01)
*A61F 2/30* (2006.01)

(52) U.S. Cl. .................... 623/17.11; 623/17.16; 606/61

(58) Field of Classification Search .. 623/17.11–17.16; 606/61, 69, 70, 71, 72, 73
See application file for complete search history.

(56) References Cited

U.S. PATENT DOCUMENTS

| 4,599,086 | A | * | 7/1986 | Doty | 606/61 |
|---|---|---|---|---|---|
| 6,063,121 | A | * | 5/2000 | Xavier et al. | 623/17.15 |
| 6,093,205 | A | * | 7/2000 | McLeod et al. | 623/17.16 |
| 6,117,135 | A | * | 9/2000 | Schlapfer | 606/61 |
| 6,120,503 | A | * | 9/2000 | Michelson | 606/61 |
| 6,156,037 | A | * | 12/2000 | LeHuec et al. | 606/61 |
| 6,190,388 | B1 | * | 2/2001 | Michelson et al. | 606/61 |
| 6,235,059 | B1 | * | 5/2001 | Benezech et al. | 623/17.16 |
| 6,576,017 | B2 | * | 6/2003 | Foley et al. | 623/17.16 |
| 6,733,531 | B1 | * | 5/2004 | Trieu | 623/17.11 |
| 2001/0020185 | A1 | * | 9/2001 | Ray | 623/17.11 |
| 2002/0120270 | A1 | * | 8/2002 | Trieu et al. | 606/61 |
| 2002/0169508 | A1 | * | 11/2002 | Songer et al. | 623/17.11 |
| 2003/0195632 | A1 | * | 10/2003 | Foley et al. | 623/17.16 |
| 2004/0098131 | A1 | * | 5/2004 | Bryan et al. | 623/17.15 |
| 2004/0143334 | A1 | * | 7/2004 | Ferree | 623/17.16 |

* cited by examiner

*Primary Examiner*—Pedro Philogene
(74) *Attorney, Agent, or Firm*—Gifford, Krass, Sprinkle, Anderson & Citkowski, PC

(57) ABSTRACT

Barriers are used to hold prosthetic components, including intradiscal devices, in position while allowing natural movement within a "safe zone." In the preferred embodiments, the barrier is in the form of a "buttress" plate coupled to a controlled linkage that prevents the device from moving into a dangerous position. The movable member(s) allow an intradiscal device to move through a safe zone while permitting mobile artificial disc replacements (ADRs) or other intradiscal devices to self-center with movement of the vertebrae. The link member(s) broadly serve as a "tether" to prevent extrusion of the intradiscal device into the spinal canal, or outside of the disc space. The intradiscal device may be mobile, or attached to one or both of the vertebral endplates. Other mechanisms to accommodate the movable link members are also disclosed. The plates are preferably constructed of metal, but the invention is not limited in terms of the biocompatible material(s) used for the plate or link members.

9 Claims, 4 Drawing Sheets

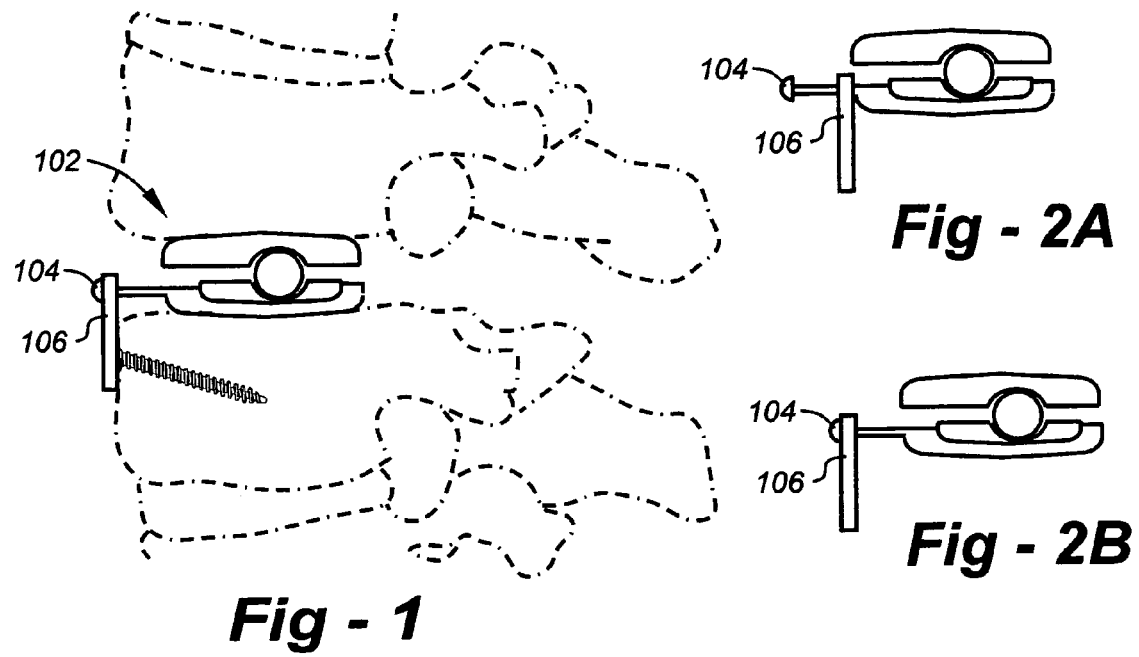
*Fig - 1*
*Fig - 2A*
*Fig - 2B*
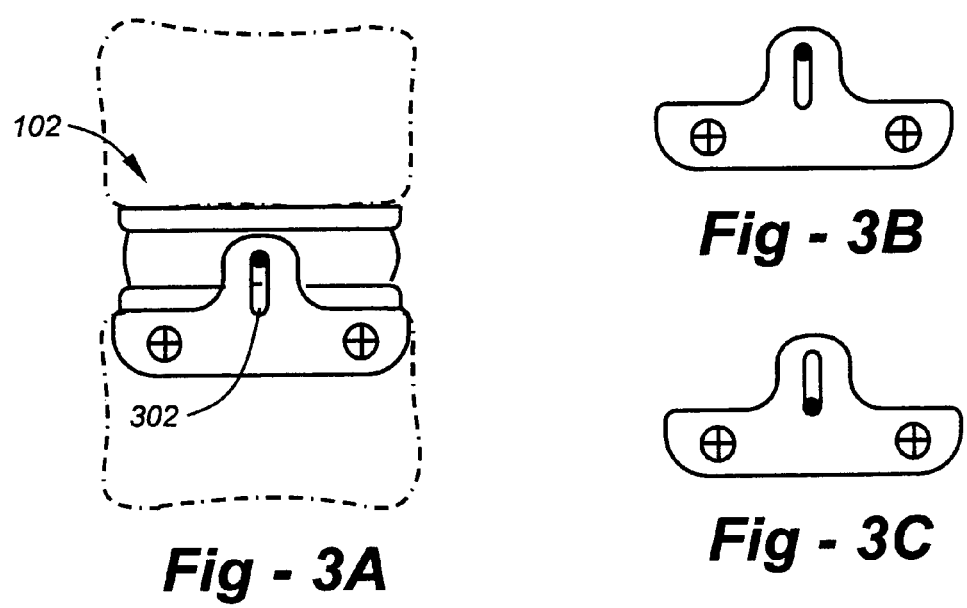
*Fig - 3A*
*Fig - 3B*
*Fig - 3C*

METHODS AND APPARATUS FOR PREVENTING THE MIGRATION OF INTRADISCAL DEVICES

REFERENCE TO RELATED APPLICATION

This application claims priority from U.S. Provisional Patent Application Ser. No. 60/376,505, filed Apr. 30, 2002, the entire content of which is incorporated herein by reference.

FIELD OF THE INVENTION

This invention relates generally to artificial intervertebral disc replacement and repair and, in particular, to apparatus for maintaining intradiscal devices in position, while allowing movement of the vertebrae and the intradiscal device independent of one another

BACKGROUND OF THE INVENTION

Seven cervical (neck), 12 thoracic, and 5 lumbar (low back) vertebrae form the normal human spine. Intervertebral discs reside between adjacent vertebra with two exceptions. First, the articulation between the first two cervical vertebrae does not contain a disc. Second, a disc lies between the last lumbar vertebra and the sacrum (a portion of the pelvis).

The spine supports the body, and protects the spinal cord and nerves. The vertebrae of the spine are also supported by ligaments, tendons, and muscles which allow movement (flexion, extension, lateral bending, and rotation). Motion between vertebrae occurs through the disc and two facet joints. The disc lies in the front or anterior portion of the spine. The facet joints lie laterally on either side of the posterior portion of the spine.

The human intervertebral disc is an oval to kidney bean shaped structure of variable size depending on the location in the spine. The outer portion of the disc is known as the annulus fibrosis. The annulus is formed of 10 to 60 fibrous bands. The fibers in the bands alternate their direction of orientation by 30 degrees between each band. The orientation serves to control vertebral motion (one half of the bands tighten to check motion when the vertebra above or below the disc are turned in either direction).

The annulus contains the nucleus pulpous, which serves to transmit and dampen axial loads. A high water content (70-80 percent) assists the nucleus in this function. The water content has a diurnal variation. The nucleus imbibes water while a person lies recumbent. Activity squeezes fluid from the disc. Nuclear material removed from the body and placed into water will imbibe water swelling to several times its normal size. The nucleus comprises roughly 50 percent of the entire disc. The nucleus contains cells (chondrocytes and fibrocytes) and proteoglycans (chondroitin sulfate and keratin sulfate). The cell density in the nucleus is on the order of 4,000 cells per micro liter.

Interestingly, the adult disc is the largest avascular structure in the human body. Given the lack of vascularity, the nucleus is not exposed to the body's immune system. Most cells in the nucleus obtain their nutrition and fluid exchange through diffusion from small blood vessels in adjacent vertebra.

The disc changes with aging. As a person ages, the water content of the disc falls from approximately 85 percent at birth to 70 percent in the elderly. The ratio of chondroitin sulfate to keratin sulfate decreases with age. The ratio of chondroitin 6 sulfate to chondroitin 4 sulfate increases with age. The distinction between the annulus and the nucleus decreases with age. These changes are known as disc degeneration. Generally disc degeneration is painless.

Nevertheless, 85 percent of the population will experience low back pain at some point. Fortunately, the majority of people recover from their back pain with a combination of benign neglect, rest, exercise, medication, physical therapy, or chiropractic care. A small percent of the population will suffer chronic low back pain. The cost of treatment of patients with spinal disorders plus the patient's lost productivity is estimated at 25 to 100 billion dollars annually.

Premature or accelerated disc degeneration is known as degenerative disc disease. A large portion of patients suffering from chronic low back pain are thought to have this condition. As the disc degenerates, the nucleus and annulus functions are compromised. The nucleus becomes thinner and less able to handle compression loads. The annulus fibers become redundant as the nucleus shrinks. The redundant annular fibers are less effective in controlling vertebral motion. The disc pathology can result in: 1) bulging of the annulus into the spinal cord or nerves; 2) narrowing of the space between the vertebra where the nerves exit; 3) tears of the annulus as abnormal loads are transmitted to the annulus and the annulus is subjected to excessive motion between vertebra; and 4) disc herniation or extrusion of the nucleus through complete annular tears.

Current surgical treatments of disc degeneration are destructive. One group of procedures removes the nucleus or a portion of the nucleus; lumbar discectomy falls in this category. A second group of procedures destroy nuclear material; Chymopapin (an enzyme) injection, laser discectomy, and thermal therapy (heat treatment to denature proteins) fall in this category. A third group, spinal fusion procedures either remove the disc or the disc's function by connecting two or more vertebra together with bone. These destructive procedures lead to acceleration of disc degeneration. The first two groups of procedures compromise the treated disc. Fusion procedures transmit additional stress to the adjacent discs. The additional stress results in premature disc degeneration of the adjacent discs.

Prosthetic disc replacement offers many advantages. The prosthetic disc attempts to eliminate a patient's pain while preserving the disc's function. Current prosthetic disc implants, however, either replace the nucleus or the nucleus and the annulus. Both types of current procedures remove the degenerated disc component to allow room for the prosthetic component. Although the use of resilient materials has been proposed, the need remains for further improvements in the way in which prosthetic components are incorporated into the disc space, and in materials to ensure strength and longevity. Such improvements are necessary, since the prosthesis may be subjected to 100,000,000 compression cycles over the life of the implant.

Migration of intradiscal devices, for example, can lead to can lead to serious injury to the tissue surrounding the disc. In particular, migration of intradiscal devices can cause injury to the spinal cord, esophagus, nerves, or the great vessels. Migration of intradiscal devices can also necessitate additional surgery to remove or replace the device.

SUMMARY OF THE INVENTION

Broadly according to this invention, barriers are used to hold intradiscal devices in position while allowing movement of the vertebrae and the intradiscal device independent of one another. In the preferred embodiments, the barrier is in the form of a "buttress" plate coupled to a controlled linkage that prevents the intradiscal device from moving into a dangerous position. That is, the movable member(s) allow the intradiscal device to move through a "safe zone," while permitting mobile artificial disc replacements (ADRs) or other intradiscal devices to self-center with movement of the vertebrae.

The link member(s) broadly serve as a "tether" to prevent extrusion of the intradiscal device into the spinal canal, or outside of the disc space. The intradiscal device may be mobile, or attached to one or both of the vertebral endplates. Other mechanisms to accommodate the movable link members are also disclosed. The plates are preferably constructed of metal, but the invention is not limited in terms of the biocompatible material(s) used for the plate or link members.

Although single tethers are described with reference to the drawings, multiple tethers may be used in all embodiments. For example, opposing lateral arrangements or anterior-posterior configurations may be used.

BRIEF DESCRIPTION OF THE DRAWINGS

FIG. 1 shows an artificial disc replacement (ADR) according to the invention;

FIG. 2A is a side-view drawing of the ADR coupled to a barrier plate through a link member;

FIG. 2B is a drawing of the configuration of FIG. 2A, showing how the link member allows the ADR to piston back and forth through a controlled range of motion;

FIG. 3A is a front-view drawing of a barrier plate;

FIG. 3B shows one extent of the vertical movement permitted by the barrier plate of FIG. 3A;

FIG. 3C shows the other extent of the vertical movement permitted by the barrier plate of FIG. 3A;

DETAILED DESCRIPTION OF THE INVENTION

Reference is now made to the drawings, wherein FIG. 1 shows an ADR 102 with an extension 104 to link the ADR to the barrier plate 106, the link member 104 may attach to both the ADR and the barrier plate. Attachment of the link member through a swivel joint to the ADR would further increase the degrees of freedom of motion. The plate and/or link member may be made of metal, polymer, or other suitable material. In addition, the screw holes in the barrier plate may contain an anti-back out feature and converge or diverge.

FIG. 2A is a side-view drawing of an artificial disc replacement (ADR) coupled to a barrier plate through a link member assuming a first position, and FIG. 2B is a drawing of the configuration of FIG. 2A showing how the link member allows the ADR to piston back and forth through a controlled range of motion.

Figure 4A:
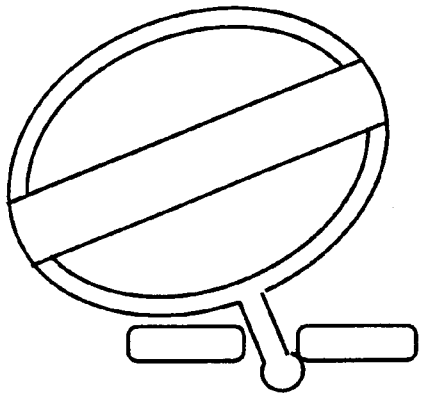
FIG. 4A is an axial cross-section of a device according to the invention.
Figure 4B:
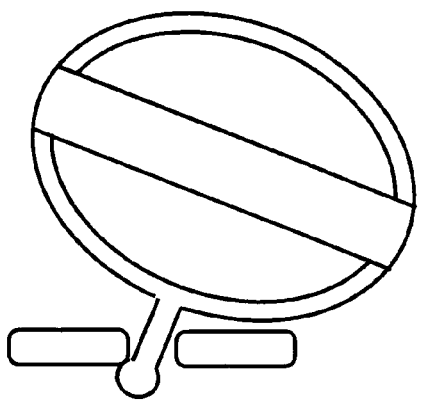
FIG. 4B shows the device of FIG. 4A moved to the other side.
Figure 5:
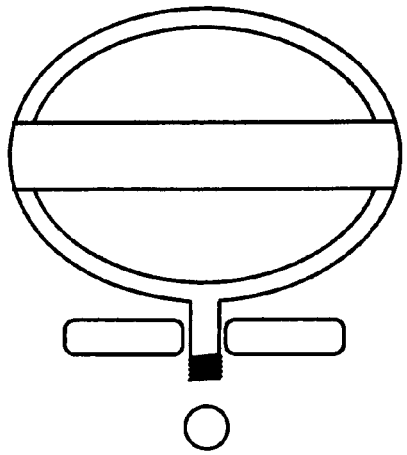
FIG. 5 is an axial cross-section showing the optional way in which an end piece may be fastened onto the link member after it is placed through the slot
Figure 6:
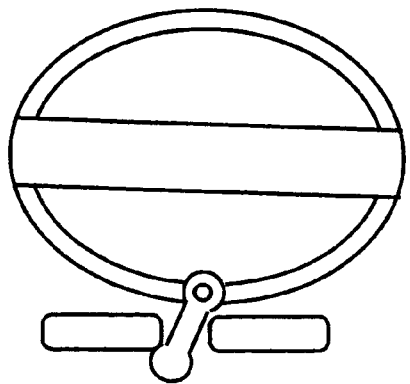
FIG. 6 is an axial cross-section showing the optional use of a swivel feature between the link member and the ADR.

FIG. 3A is a front-view drawing of a barrier plate 302 having a slot which permits vertical movement and angulation. FIG. 3B shows one extent of the vertical movement permitted by the barrier plate of FIG. 3A, and FIG. 3C shows the other extent of the vertical movement permitted by the barrier plate of FIG. 3A. FIG. 4A is an axial cross-section of a device according to the invention, illustrating the way in which the use of a barrier plate and link member affords a controlled range of side-to-side motion. FIG. 4B shows the device of FIG. 4A moved to the other side. FIG. 5 is an axial cross-section showing the optional way in which an end piece may be fastened onto the link member after it is placed through the slot. FIG. 6 is an axial cross-section showing the optional use of a swivel feature between the link member and the ADR.

Figure 7A:
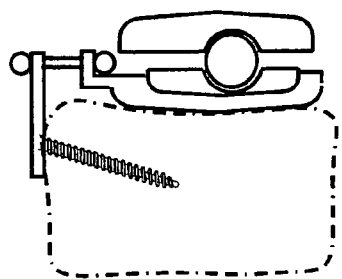
FIG. 7A is a side-view drawing showing the use of a cable link member in an extended position.
Figure 7B:
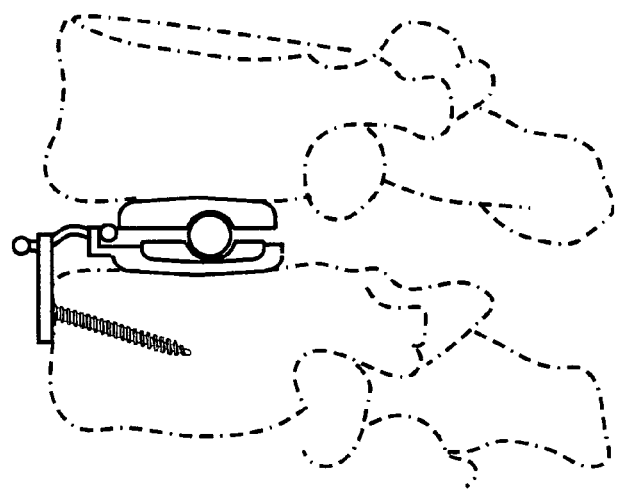
FIG. 7B shows the cable link member of FIG. 7A in a contracted state.
Figure 8A:
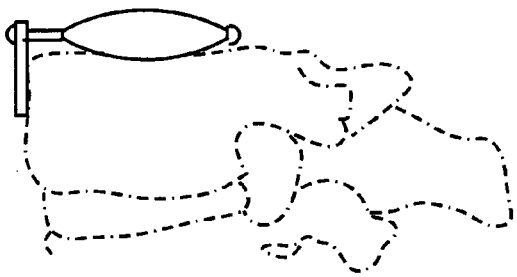
FIG. 8A shows the option of extending the link member through the device.
Figure 8B:
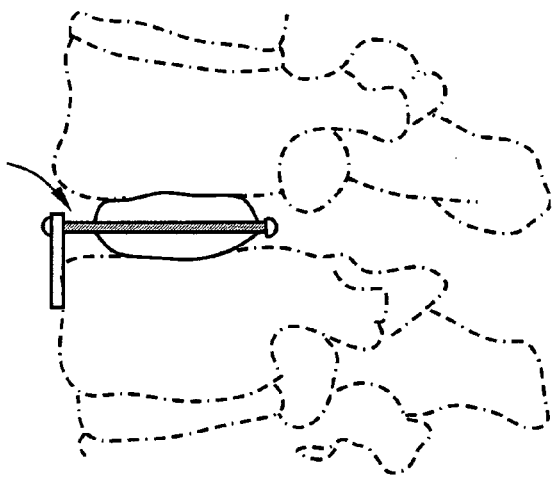
FIG. 8B is a cross-section of the device of FIG. 8A.

While, in the preferred embodiment, the link member is at least partially rigid, flexible link members may also be used. FIG. 7A is a side-view drawing showing the use of a cable link member in an extended position. FIG. 7B shows the cable link member of FIG. 7A in a contracted state. Additionally, although the link member attach to an anterior portion of an ADR or other device, it may extend through the device, as shown in FIG. 8A. FIG. 8B is a cross-section of the device of FIG. 8A.

Figure 9:
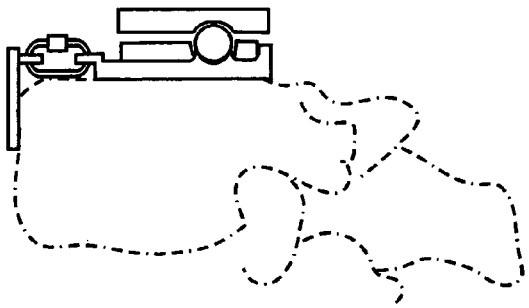
FIG. 9 is a drawing which shows yet a different alternative embodiment, wherein the link member utilizes a threaded chain link.

FIG. 9 is a drawing which shows yet a different alternative embodiment, wherein the link member utilizes a threaded chain link, not unlike a key chain. In this end, the other flexible link member embodiments, freedom of motion is permitted in all directions (apart from the areas outside of the safe zone).

Figure 10:
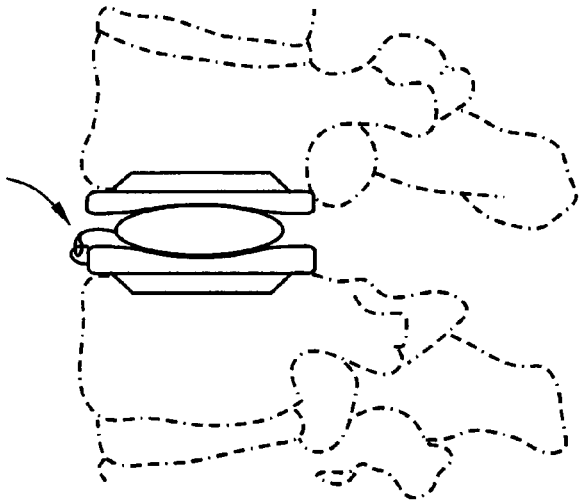
FIG. 10 is a sagittal cross section of the spine, an ADR, and another embodiment of a device according to the invention.

FIG. 10 is a sagittal cross section of the spine, an ADR, and another embodiment of a device according to the invention. The disc spacer is connected to ADR endplate by a flexible link member.

Figure 11:
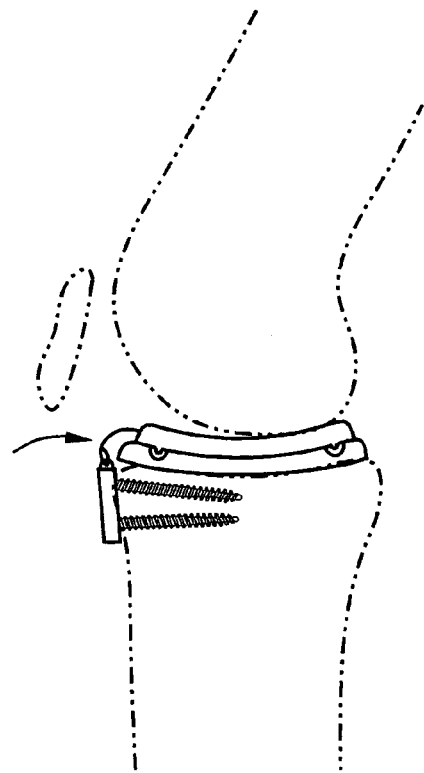
FIG. 11 is a sagittal cross section of the knee, a knee spacer, and another embodiment.

FIG. 11 is a sagittal cross section of the knee, a knee spacer, and another embodiment. The knee spacer is connected to a plate by a flexible member 1102. The plate is attached to the tibia. The screws are locked to the plate. Mechanisms to lock screws to plates are well known to those skilled in the art. The screws can diverge or converge to improve pull out strength.

Figure 12:
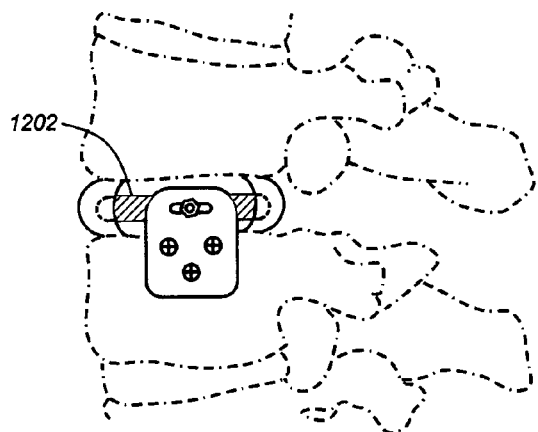
FIG. 12 is a view of the lateral aspect of the lumbar spine and a further alternative embodiment.

FIG. 12 is a view of the lateral aspect of the lumbar spine and a further alternative embodiment. Note that the component 1202 of the device that fits behind the annulus fibrosis is free to rotate and slide relative to the plate component of the device.

Figure 13:
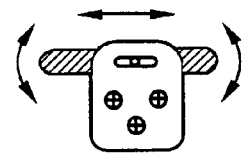
FIG. 13 shows a device without a nut that holds the intradiscal component to the plate component.

FIG. 13 is a view of a device without a nut that holds the intradiscal component to the plate component. As noted above the intradiscal component is free to slide and rotate relative to the plate component. This motion may help accommodate spinal motion. For example, flexion and extension of the spine would be easier if the new embodiment of the device was used on the lateral aspect of the lumbar spine.

Figure 14:
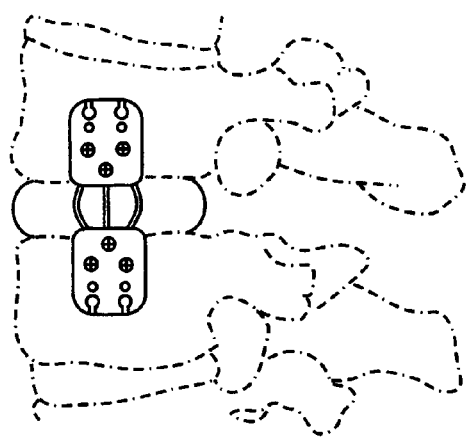
FIG. 14 is a view of the lateral aspect of the spine and a different alternative embodiment of the invention.

FIG. 14 is a view of the lateral aspect of the spine and a different alternative embodiment of the invention. Cables or other flexible members are connected to plate components on the vertebrae on either side of the disc.

Figure 15:
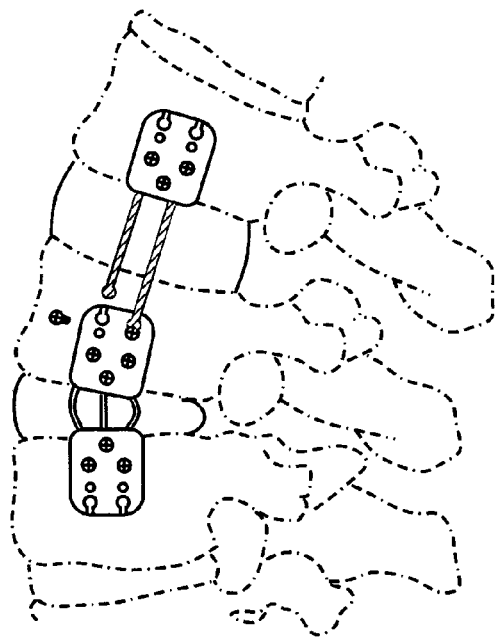
FIG. 15 is a view of the lateral aspect of the lumbar spine and the device drawn in FIG. 14.

FIG. 15 is a view of the lateral aspect of the lumbar spine and the device drawn in FIG. 14. The drawing illustrates the lumbar spine in an extended position. The slack in the anterior cable of the lower device has been decreased. The slack in the posterior cable of the lower device has been increased. The figure also illustrates a method for connecting an adjacent vertebra at a later date. As illustrated by the upper device, a ball shaped end of the new cables can be fitted into slots in the plate component. The cables can be held in position by one or more screws that fit over the ball portion of the cable and into the plate.

Figure 16:
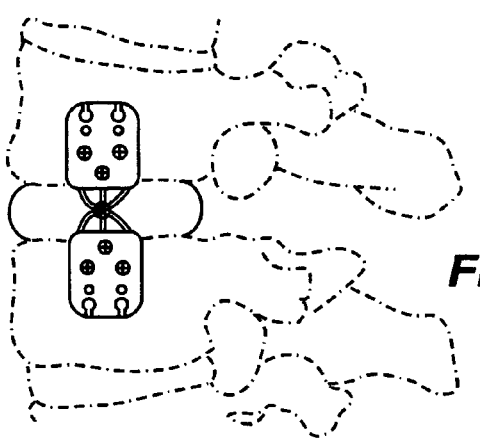
FIG. 16 is a view of the lateral aspect of the lumbar spine and an alternative embodiment using cross-coupled cables.
Figure 17:
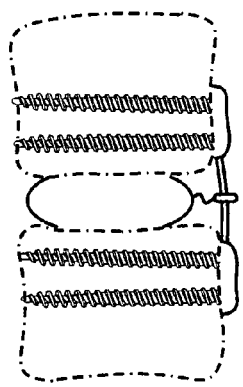
FIG. 17 is a view of the anterior aspect of the spine, the embodiment of the device drawn in FIG. 16, and an artificial disc replacement linked to the device.

FIG. 16 is a view of the lateral aspect of the lumbar spine and an alternative embodiment using cables that are cross coupled similar to those in my issued U.S. Pat. No. 6,248,106, incorporated herein by reference. The device can also hold one end of the link member as shown in U.S. Provisional Application Serial No. 60/376,505, incorporated herein by reference. FIG. 17 is a view of the anterior aspect of the spine, the embodiment of the device drawn in FIG. 16, and an artificial disc replacement linked to the device.

I claim:

1. Apparatus for limiting the movement of a prosthetic device situated between opposing bones, comprising:
   an articulating device;
   an anchoring unit adapted for fastening to at least one of the bones; and
   a link member coupling the articulating device to the anchoring unit, thereby facilitating a limited degree of movement of the device.

2. The apparatus of claim 1, wherein:
   the anchoring unit is adapted for fastening to a vertebra; and
   the articulating device is an intradiscal device.

3. The apparatus of claim 2, wherein the link member facilitates a limited degree of anterior-posterior motion of the intradiscal device.

4. The apparatus of claim 2, wherein the link member facilities a limited degree of lateral motion of the intradiscal device.

5. The apparatus of claim 1, wherein the link member is substantially rigid.

6. The apparatus of claim 1, wherein the link member is flexible or chain-like.

7. The apparatus of claim 1, wherein the articulating device is an artificial disk replacement (ADR).

8. The apparatus of claim 1, wherein the anchoring unit is a plate adapted for fastening to at least one of the bones.

9. The apparatus of claim 8, wherein the plate is adapted for fastening to the anterior portion of a vertebra.

* * * * *